United States Patent [19]

Golub et al.

[11] Patent Number: 4,666,897
[45] Date of Patent: May 19, 1987

[54] INHIBITION OF MAMMALIAN COLLAGENOLYTIC ENZYMES BY TETRACYCLINES

[75] Inventors: Lorne M. Golub, Smithtown; Thomas F. McNamara, Port Jefferson; N. S. Ramamurthy, Smithtown, all of N.Y.

[73] Assignee: Research Foundation of State University, Albany, N.Y.

[21] Appl. No.: 566,517

[22] Filed: Dec. 29, 1983

[51] Int. Cl.$^4$ .............................................. A61K 31/65
[52] U.S. Cl. .................................................... 514/152
[58] Field of Search .......................... 424/227; 514/152

[56] References Cited

U.S. PATENT DOCUMENTS

| | | | |
|---|---|---|---|
| 2,895,880 | 7/1959 | Rosenthal | 424/227 |
| 4,248,892 | 2/1981 | Kanamaru et al. | 424/317 |
| 4,371,465 | 2/1983 | McGregor | 424/177 |
| 4,457,936 | 7/1984 | Draeger et al. | 424/270 |

OTHER PUBLICATIONS

Bauer, et al., 1983, J. Invest. Dermatol., vol. 81, pp. 162, 163 168.
Harris, et al., 1984, Collagen Rel. Res., vol. 4, p. 493.
Berman and Manabe, 1973, Ann. Ophthalmol., Nov., p. 1193.
Golub, et al., 1985, J. Periodontal Res., vol. 20, pp. 12–23.
Welgus and Stricklin, 1983, J. Biol. Chem., vol. 258, p. 12259.
Uitto, et al., 1984, J. Oral. Path., vol. 13, p. 412.
Narayanan and Page., 1983, Collagen Rel. Res., vol. 3, p. 54.
Golub, et al., 1985, J. Periodontal. Res., Special Issue, p. 93.
Vater, et al., 1978, J. Clin. Invest., vol. 62, p. 987.
Harris, et al., 1984, Collagen Rel. Res., vol. 4, pp. 504–505.
Cowen, et al., 1985, Biochem. International, vol. 11, p. 273.
Belaisse, et al., 1985, Biochem. Biophys. Res. Commun., vol. 133, p. 483.
Golub, et al., 1983, J. Periodontal Res., vol. 18, pp. 516–526.
Chemical Abstracts 100:96203a (1983).
Chemical Abstracts, 93:142977t (1980).
Chemical Abstracts, 76:30596k (1969).
Dreisbach et al., Induction of Collagenase Production in Vibrio B-30, J. Bacteriol, vol. 135, No. 2 (1978) pp. 521–527.
Goodman and Gilman, The Pharmacological Basis of Therapeutics, 6th ed., pp. 961–962 (1980).

*Primary Examiner*—Albert T. Meyers
*Assistant Examiner*—John M. Kilcoyne
*Attorney, Agent, or Firm*—Omri M. Behr

[57] ABSTRACT

A method of reducing pathologically excessive levels of activity of collagenolytic enzymes in mammals to substantially normal levels by administering 10-100% of the normal antibiotic therapeutic dose of a tetracycline is disclosed.

10 Claims, 8 Drawing Figures

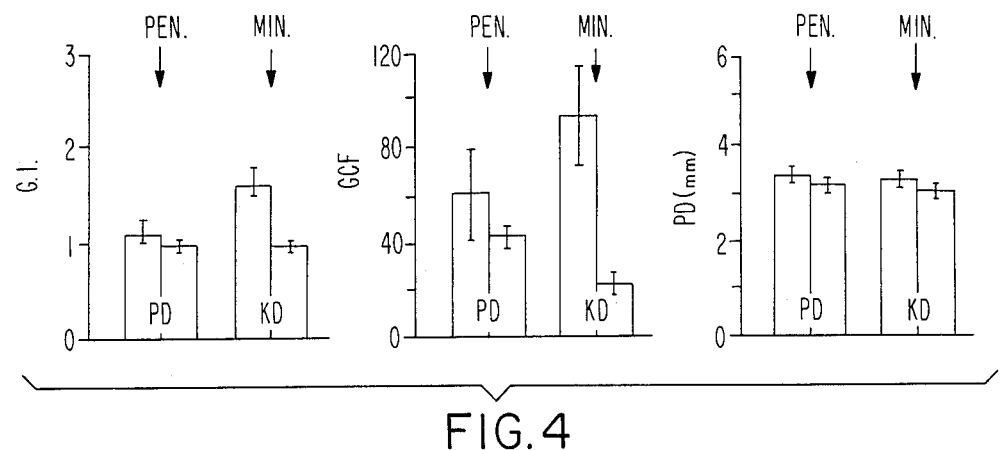
FIG. 4
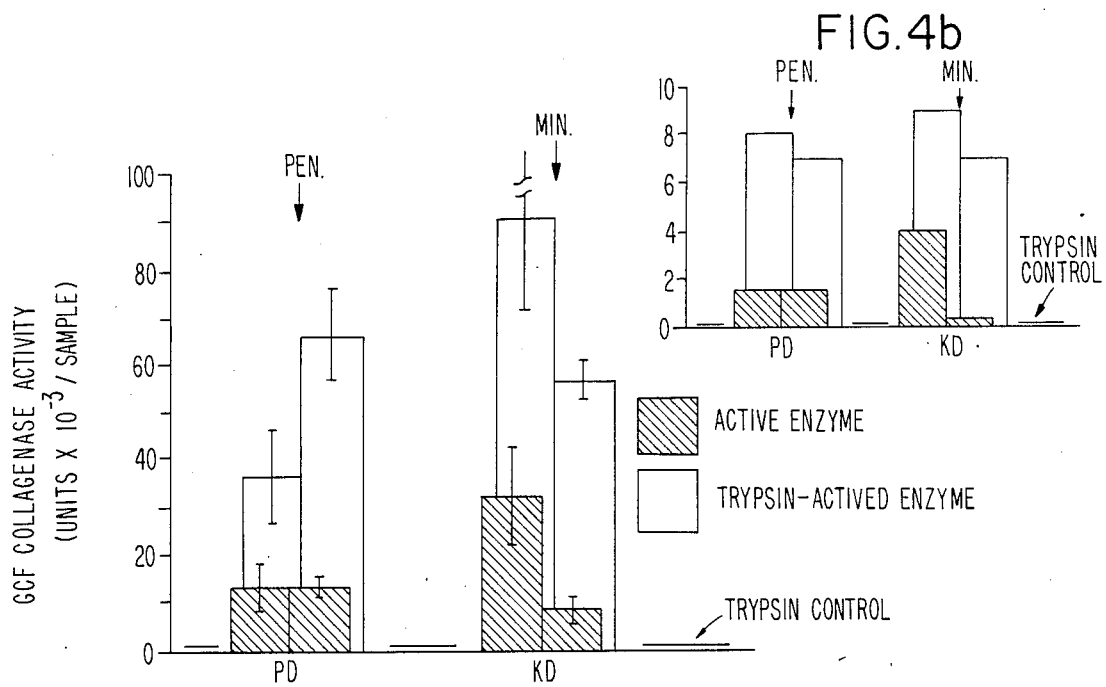
FIG. 4a
FIG. 4b

INHIBITION OF MAMMALIAN COLLAGENOLYTIC ENZYMES BY TETRACYCLINES

BACKGROUND OF THE INVENTION

Collagenase is an enzyme normally present in mammals. The enzyme, which is produced in a number of body tissues and cells, degrades collagen, (the major structural protein of connective tissues, such as those in bone, skin, tendon and gingiva) normally during connective tissue remodeling. However, when collagenase, is produced in excessive amounts, then the pathologic destruction of these tissues is the result. This excessive collagenase production has been observed to occur in a number of disease states such as hyperparathyroidism, diabetes, periodontal disease and rheumatoid arthritis. The results of excess collagenolysis are serious and debilitating, such as excessive resorption of bone associated with hyperparathyroidism, the ulceration of the cornea, the destruction of joint tissue associated with rheumatoid arthritis, and the breakdown of the gingival collagen fibers and the bony socket associated with periodontal disease.

In recent years, tetracycline has been advocated as an adjunct in the treatment of periodontal diseases, including chronic periodontitis in the adult (Fasciano and Fazio, *Quintessence International,* October, #10, 1081–1088 (1981)) and more often, for rapidly progressing juvenile periodontitis (Slots, et al., *J. Peridontol,* 50, 405–509 (1979)); Genco, et al., *J. Dent. Res.* 60, Special Issue A, Abstract 872 (1981). Its therapeutic efficacy has been attributed solely to the drug's antimicrobial activity particularly against specific Gram-negative organisms believed to be the cause of these diseases (Genco, *J. Periodontol,* 52, 545–558 (1981)). Recently, Williams, et al., *J. Peridontal Res.*, 16, 666–674 (1981) described a significant improvement in periodontal disease in dogs on long-term tetracycline therapy, an effect that did not appear to correlate with expected shifts in the crevicular microflora. Williams, et. al. concluded that the beneficial effect of tetracycline must have resulted from the suppression of a strain of bacteria that was not measured in their study. Similar clinical changes were observed in a limited number of human subjects. Tetracycline therapy in periodontal disease has also been evaluated by Ciancio, *J. Periodontol.,* 43, 155–159 (1976) and Ciancio, et al., *J. Periodontol.,* 51, 531–534 (1980). Kornman & Karl, (1982, *J. Periodontol.,* 53, 604–610) reported that the long-term use of tetracycline was clinically beneficial in patients who did not respond to routine periodontal therapy (debridement by instrumentation). In all of these studies, the only perceived value of tetracyclines is an antibacterial drug.

Diabetes in rats and humans has been found to increase tissue collagenase activity. Evidence for this effect was seen in extracts of gingiva and skin (Ramamurthy and Golub, *J. Periodontal Res.,* 18., 31–39 (1983)) and in cultures of gingival tissue (Ramamurthy, et al., *J. Periodontal Res.,* 9, 199–206 (1974); Golub, et al., *J. Dent. Res.,* 57, 520–525, 1978; Kaplan, et al., *J. Dent. Res.,* 61, Special Issue, 275 (1982)). Unusually severe periodontal disease which occurs during diabetes in man (Finestone and Boorujy, *Diabetes,* 16, 336–340, 1967; Cianciola, et al., *J.A.D.A.,* 104, 653–660 (1982)) and experimental animals (Bissada, et al., *Periodontics.,* 4, 223 (1966)), reflects accelerated collagen breakdown which could be mediated by the excessive collagenase generated during this systemic disease. It has been suggested that the overgrowth of Gram-negative organisms in the gingival crevice of the diabetic rat could, by generating excessive endotoxin in the area, be the cause of the abnormally high collagenase levels in the gingiva (McNamara et al., *Archs. Oral Biol.,* 27, 217–223 (1982)).

Additionally, it has been reported that tetracycline is effective in the treatment of rheumatoid arthritis (Brown, et al., *Comp. Pathol. Zoo Animals,* (eds. Montali & Migaki), Smithsonian Institution Press, 259–266 (1980)). Brown's sole rationale for the use of these antibiotics is to eliminate infection of the joint tissues with the "mycoplasma group of microorganisms which he believes is the cause of arthritis. However, there has been heretofore no recognition of the ability of tetracycline to reduce pathologically excessive levels of collagenolytic enzyme(s) (such as collagenase) activity to substantially normal levels.

SUMMARY OF THE INVENTION

The present invention relates to a method of reducing pathologically excessive amounts of collagenolytic enzyme(s) activity in a mammalian system. More particularly, this invention relates to a method of reducing such excess collagenase or other collagenolytic enzymes such as elastase or gelatinase to substantially normal levels which comprises administering to mammals in need of anti-collagenase therapy an anti-collagenase effective amount of a tetracycline.

For convenience sake, the presently marketed dosage forms of the various tetracyclines may be utilized in the method of the present invention without substantial change. This is especially facilitative to the practice of the invention. Tetracyclines and their various dosage forms have been utilized for many years and the side effects from such dosage forms are well studied, well recognized, and minimized by the said dosage forms.

The method of the present invention involving reducing excessive collagenolytic enzyme activity levels to normal levels can be used to treat conditions in a number of diseases, including rheumatoid arthritis, periodontal disease and ulcerated corneae. These disease states (and others) all exhibit the pathological effects of excessive collagenase levels which include excessive resorption of bone, destruction of joint tissue, breakdown of the gingival collagen fibers and the bony sockets, and ulceration of the cornea, as well as other destruction of collagen containing tissue. While other manifestations of these disease states may be treated with supplementary drugs, i.e., inflammation in rheumatoid arthritis, or infection in periodontal disease, the use of the tetracycline will serve to reduce the excessive collagenase levels and collagenolytic activity to a normal level. This anti-collagenase thereapy is valuable supplementary aid for use by a medical practitioner in the treatment and control of such diseases as described above.

BRIEF DESCRIPTION OF THE DRAWINGS

FIG. I (a & b) are block graphs of a) Collagenolytic activity, and b) bone loss in conventional diabetic rats.

FIG. II (a & b) are similar to FIG. I, a & b except that the rats are also germ-free.

Figure 1B:
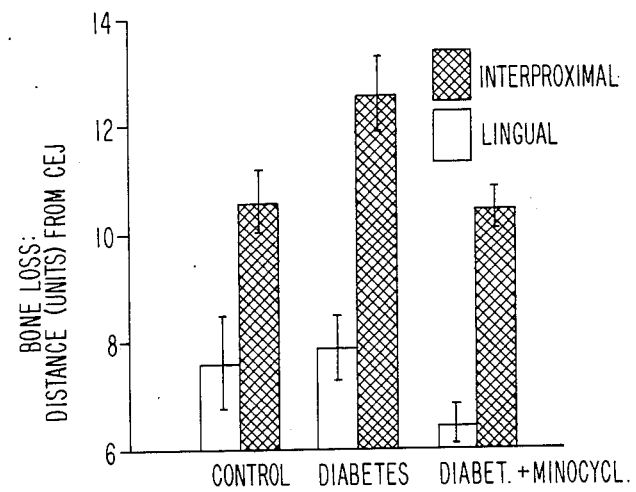
Figure 1A:
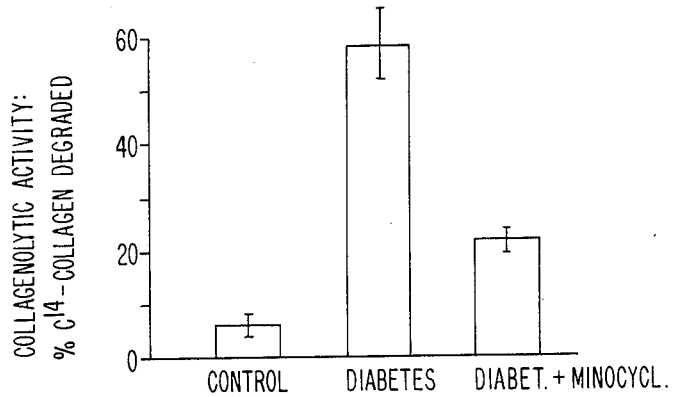
Figure 2B:
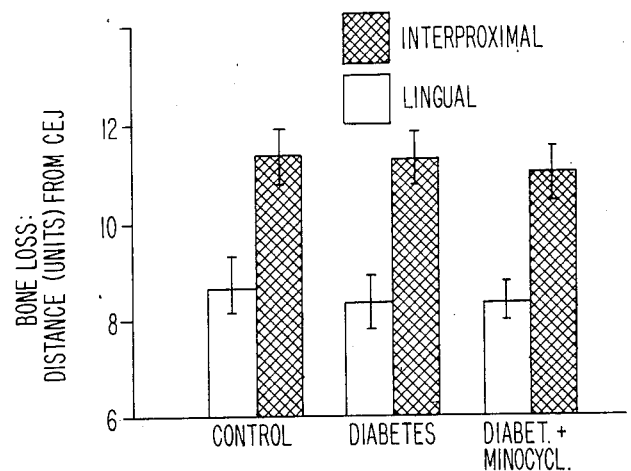
Figure 2A:
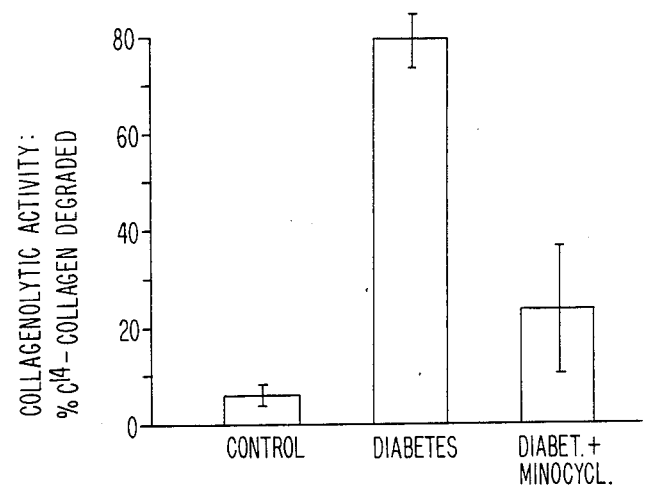
Figure 3:
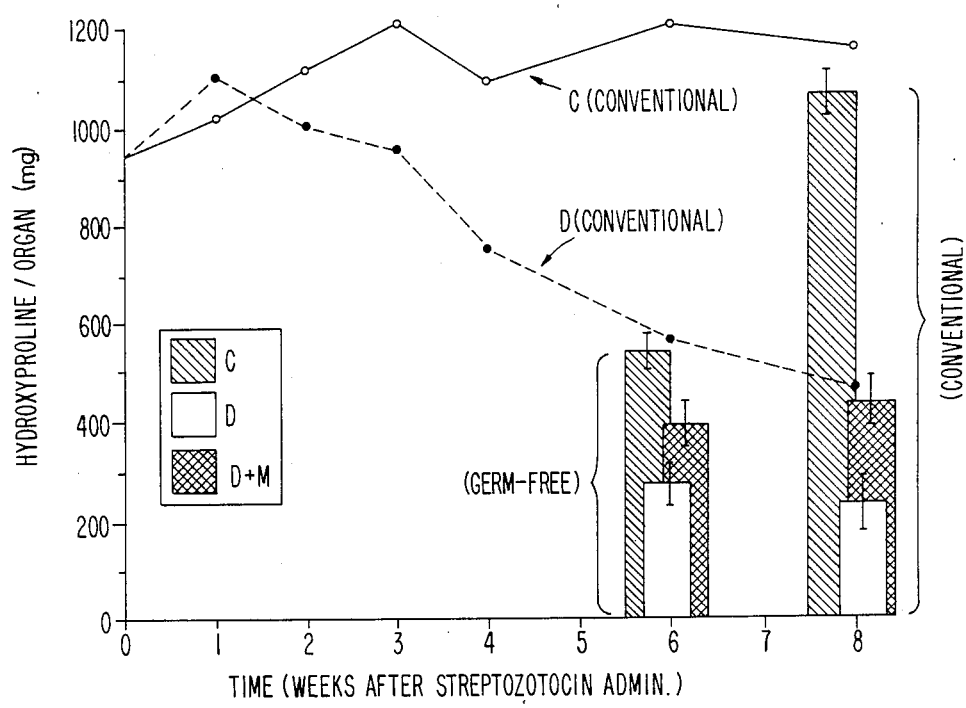

FIG. III shows the effect of minocycline on the skin collagen levels of streptozotocin diabetic rats.

FIG. IV shows the effects of penicillin and minocycline on gingival disease and on GCF collagenolytic activity in twin young diabetic males.

DESCRIPTION OF THE PREFERRED EMBODIMENTS

The tetracycline utilized in the present invention may be any of the readily available, pharmaceutically acceptable tetracycline known in the medical art. Included in this group of tetracyclines are those such as chlortetracycline, which is marketed under the tradename Acronize, Aureocina, Aureomycin, Biomitsin, Biomycin and Chrysomykine; Demeclyeycline marketed as Ledermycin, Detravis, Meciclin, and Mexocine; Doxycycline marketed as Vibramycin, Vibramycin Hyclace, Liomycin Vibradox, Panamycin, Titradox, Hydramycin, Tecacin; Lymecycline which is marketed as Armyl, Mucomycin, Tetramyl, Tetralysal; Methacycline which is marketed as Adriamicina, Cyclobiotic, Germicilclin, Globociclina, Megamycine, Pindex, Londomycin, Optimycin, Rondomycin; Minocycline which is marketed as Minocin, Klinomycin, Vectrin; Oxytetracycline which is marketed Biostat, Oxacycline, Oxatets, Oxydon, Oxymycin, Oxytan, Oxytetracid, Ryomycin, Stezazin, Tetraject, Terramycin, Tetramel, Tetran, Dendarcin, Dendrcin; Rolitetracycline marketed as Bristacin, Reverin, Superciclin, Syntetrex, Syntetrin, Synotodecin, Tetraverin, Transcycline, Velacicline, Velacycline; and Tetracycline marketed as Achromycin, Ambramycin, Cyclomycin, Polycycline, Tetrabon, and Tetracyn.

The active salts, which are formed through protonation of the dimethylamino group on carbon atom 4, exist as crystalline compounds and are very viable in water. However, these amphoteric antibiotics will crystallize out of aqueous solutions of their salts unless stabilized by an excess of acid. The hydrochloride salts are used most commonly for oral administration and are usually encapsulated because of their bitter taste. Water soluble salts may be obtained also from bases such as sodium or potassium hydroxides but are not stable in aqueous solution, they are also formed with divalent and polyvalent metals, these forms, though operative are not preferred.

The tetracyclines used in the method of the present invention are preferably administered at a dosage level of from 10 to 100%, suitably 20-80%, of the normal antibiotic therapeutic dose of the particular tetracycline compound being employed. By normal antibiotic therapeutic dose is meant the dosage of the particular tetracycline compound which is commonly used and recommended for the treatment of bacterial infection. More than 100% of the normal antibiotic therapeutic dose may be utilized in the method of the present invention but there is no particular advantage in doing so and such over-dosage may in fact lead to complications.

The present invention is intended for use as long term (as well as short-term, or even episodic) therapy. The long term administration of tetracyclines at antibiotically effective dose levels may have a negative effect on healthy flora such as intestinal flora and may also lead to the production of resistant organisms. These disadvantages are substantially reduced by the use of sub-antibiotic dosages.

The normal antibiotic therapeutic dose of the tetracycline is, for the most part, well studied and well documented so that few, if any, side effects other than those mentioned above can be anticipated in using this safe dosage level for the reduction of excess collagenase to a normal collagenase level. For instance, the normal and usual dose of tetracycline is, orally, the equivalent of 250 mg. of tetracycline hydrochloride 4 times daily; intramuscular, the equivalent of 100 mg. of tetracycline hydrochloride 2 or 3 times daily; intravenous infusion, the equivalent of 250-500 mg. of tetracycline hydrochloride over a period of ½ to 1 hour, twice daily. And the usual dosage range, orally, is the equivalent of 1-4 g. of tetracycline hydrochloride daily; intramuscularly, the equivalent of 200-500 mg. of tetracycline hydrochloride daily; and intravenously, the equivalent of 500 mg. to 2 g. of tetracycline hydrochloride daily.

For rolitetracycline, the usual dose range is intramuscularly, 150-350 mg. every 12 hours; and intravenously, 350-700 mg. every 12 hours. For chlortetracycline the usual daily dose range is 250-500 mg.

When oxytetracycline is utilized the usual dose is, orally, 250 mg. 4 times daily; intra-muscularly, 100 mg. 2 or 3 times daily; intravenously, 250-500 mg. over a period of ½ to 1 hour twice daily. The usual dose range is orally, 1 to 4 g. daily; intramuscularly, 200-500 mg. daily; intravenously 500 mg. to 2 g. daily.

For methacycline the usual dose is 600 mg. of the hydrochloride salt or 560 mg. of methacycline base, daily in divided doses. When demeclocycline is utilized the usual dose is 600 mg. daily in 4 divided doses of 150 mg. or 2 divided doses of 300 mg. each, and the usual dose range is from 150-900 mg. per day. Doxycycline is typically utilized in a dosage of 100 mg. every 12 hours during the first day of treatment followed by a maintenance dose of 100 mg. daily.

The method of the present invention utilizes pharmaceutical compositions which incorporate the particular tetracycline being utilized. For oral administration the tetracyclines utilized in this invention may be formulated in the form of tablets, capsules, elixirs or the like. For parenteral administration they may be formulated into solutions or suspensions or intramuscular injections, or additionally, the tetracyclines of the present invention may be reasonably incorporated into a polymer carrier delivery system for use topically or locally, specifically in cases of periodontal diseases or to be delivered topically directly into the periodontal pocket by some other technique (e.g. by the patient using the Water-Pik home care device or by the dentist using an ultrasonic (cavitron) system. The dosage of tetracyclines administered in the present invention is also additionally dependent upon the age and weight of the animal species being treated, the mode of administration, and the type and severity of the excess collagenase induced disease being treated.

The following discussion describes in detail compositions and methods illustrative of the present invention. It will be apparent to those skilled in the art that many modifications, both of materials and methods, may be practiced without departing from the purpose and intent of this disclosure.

EXPERIMENTAL

EXAMPLE I a)

The reduction of collagenolytic enzyme(s) Activity in Test Animals (a) Conventional Rats Five month old (mean weight, 445g) male Sprague Dawley rats were made diabetic by I.V. injection of streptozotocin (70 mg/kg body weight), after a 12 hour fasting period, (as described by Golub, et al., *Biochim. Biophys. Acta.*, 534, 73–81 (1978) and Golub, et al., *Infect. Immun.*, 37, 1013–1020 (1982). Age matched uninjected rats served as controls. Some of the diabetic rats received the tetracycline, minocycline (20 mg. Minocin ® per day; Lederle Laboratories, Pearl River, N.Y.), by gavage on a daily basis beginning 3 days after diabetes is induced. After a 25 day experimental period, blood samples were taken for glucose analysis, and subgingival plaque samples were taken for assessment of the microflora in the region (McNamara, et. al., *Archs. Oral. Biol.*, 27, 217–223 (1982)). The animals were then sacrificed, gingival samples were taken for tissue culture and the jaw bones dissected. The results are set forth below and illustrated in FIG. I.

To test the effect of physiologic levels of minocycline (the concentration in human serum, during a therapeutic regimen, is approximately 2 ug/ml; that in the gingival crevicular fluid is 4–5 times greater; Ciancio, et. al., 1980, *J. Periodontol.*, 51, 531–534) on mammalian collagenolytic activity in vitro, peritonealexudate polymorphonuclear leucocytes (PMNLs) were collected from 15 mole (non-diabetic) rats 4 hours after I.P. injection of 0.15% glycogen. An extract of PMNLs was prepared, 250 μl aliquots of this extract were incubated with $^{14}$C-glycine labeled collagen fibrils for 14 hours at 35° C. (in the presence or absence of minocycline, or EDTA, or additional $CaCl_2$), and collagenolytic activity was measured as described by Nicoll, et al., (*Experientia.*, 37, 315–317).

(b) Germ-free rats

In a second separate procedure, germfree rats (purchased from Taconic Farms, Germantown, N.Y.), were maintained in inflatable vinyl isolators (Standard Safety Equipment Co., Palatine, Ill ), until a weight of 360 g±15 was reached. At this time (6 weeks after purchase), diabetes was induced in some of the animals, as described above in a), and the control and diabetic animals maintained under germfree conditions for an additional 6 weeks prior to sacrifice. Half of the diabetic animals received minocycline (Minocin ®) (20 mg/day) by gavage for the last 4 weeks of the protocol. Blood and tissues were then obtained to assess gingival collagenolytic enzyme activity and the loss of skin collagen and bone. The results are set forth below and illustrated in FIG. II.

(c) Results

Alveolar bone loss was assessed in the right and left mandibles of both the conventional and germfree rats (control and diabetic) using a modification of a previously described technique (Stralfors, et.al,, *Archs. Oral. Biol.*, 12, 1213–1216 (1967); Heijl, et. al., *J. Periodontal Res.*, 15, 405–419 (1980)). The mandibles were defleshed (autoclaving followed by soaking in 2N NaOH for 2–3 h), dried, and the distance (expressed as units; 1 unit=0.05 mm) between the cementoenamel junction (CEJ) and the crest of the alveolar bone is measured in the long axis of the root surface at 10 specified sites on lingual surfaces of the 3 molar teeth (see Crawford, et.al., *J. Periodontal Res.*, 13, 316–325 (1978)) using an eye-piece micrometer in a dissecting microscope (20× magnification).

Because uncontrolled diabetes in the rat results in the massive resorption of skin collagen associated with increased collagenase activity in this tissue, the collagen content of entire skins from the germfree and from the conventional control and diabetic rats, including those treated with minocycline was measured. The techniques used were those described by Schneir and Golub, (*Streptozotocin: Fundamentals and Therapy* (Ed. M. K. Agarwal, Elsevier/North-Holland Biomed Press, Chapter 12, pp 161–182, (1981)).

The techniques used to measure the collagenolytic enzyme activity of gingival tissue in culture, and in polymorphonuclear leucocytes (PMNLs), are those described by Golub, et. al., (*J. Dent. Res.*, 57, 520–525 (197)8) and Nicoll, et. al., (*Experimentia*, 37, 315–317, (1981)) with minor modifications.

The conventional and germfree control rats were found to exhibit relatively low blood glucose concentrations ranging from 85 to 186 mg % (mean=141 mg %±14). As expected, the diabetic conventional and germfree rats, with or without minocycline therapy, exhibited severe hyperglycemia having blood glucose vales ranging from 310 to 832 mg%, with a mean of 503 mg %±42. The germfree rats and isolators showed negative results for aerobic and anaerobic cultures throughout the experimental period, and treatment of the conventional diabetic rats with the tetracycline minocycline eliminated detectable signs of a Gram-negative microflora in the gingival crevices.

The gingiva from the conventional and germfree control rats produced minimal collagenolytic activity in tissue culture; less than 10% of the $^{14}$C-collagen fibrils were found to be degraded after 3 days in culture (see FIGS. Ia and IIa). In contrast, collagenolytic activity was markedly increased in gingiva from the diabetic rats, under both conventional (see FIG. Ia) and germfree (see FIG. IIa) conditions. Administering the tetracycline minocycline orally on a daily basis reduced the gingival collagenolytic activity in both diabetic conventional and germfree rats by 62% and 70% respectively (see FIG. Ia and IIa).

Diabetes in the conventional rats produced a slight, but significant, increase (p>0.05) in bone loss in the interproximal region, compared to controls; this effect was completely reversed by the tetracycline administration (see FIG. Ib). The patterns of change on the lingual surfaces of the mandibles were similar; however, these effects are not found to be statistically significant. In the germfree rats, no differences in bone levels could be detected between the three groups (see FIG. IIb), however significant changes are seen in skin (see FIG. III). Diabetes in the germ-free rats (6 weeks after inducing diabetes with streptozotocin) resulted in a 48% reduction in skin collagen content compared to the germ-free control rats (p>0.01), and minocycline treatment of the germ-free diabetics increased the collagen levels in this tissue by 45% (p>0.05). Similar patterns of change in skin collagen content were seen in conventional control, conventional diabetic, and conventional minocycline-treated diabetic rats (see modified FIG. III).

The collagenolytic activity in the leucocyte (or PMNL) extract was completely inihibited by EDTA (mammalian collagenase is a calcium dependent neutral protease; (see Sellers and Murphy, *Int. Rev. Conn. Tiss. Res.*, 9, 151–189 (1981)), and the collagen substrate was not susceptible to non-specific proteolysis by trypsin (see Table I). Minocycline, in concentrations approximately those found in human serum and gingival crevicular fluid (Ciancio, et. al., *J. Periodontal*, 51, 531–534 (1980)), produced almost complete inhibition of PMNL collagenase activity, an effect which was reversed by increasing concentrations of calcium (See Table I). Two non-tetracycline antibiotics (penicillin - streptomycin) similarly tested were found to have no detectable effect on collagenase (Table I).

In a similar but separate experiment, the effect of four (4) different types of tetracyclines on PMNL collagenolytic activity was tested (Table 2). All of the tetracyclines inhibited this mammalian collagenolytic activity, whereas two additional non-tetracycline antibiotics (ampicillin and cefazolin) were again found to be ineffective against this enzyme(s).

TABLE 1

The Effect of Minocycline on rat PMNL Collagenolytic Activity in vitro

| Incubation Mixture | | Collagenolytic Activity:*  % $^{14}$C—collagen gel lysed |
|---|---|---|
| PMNL extract (control)** | 1 | 85.5 |
| PMNL extract + EDTA (54 mM) | 2 | 3.1 |
| Trypsin (1 μg) | 3 | 2.6 |
| Bacterial collagenase (250 μg) | 4 | 88.7 |
| PMNL extract + Minocin (5 μg/ml) | 5 | 12.4 |
| PMNL extract + Minocin (20 μg/ml) | 6 | 8.3 |
| Above, (6.) + CaCl$_2$ (10 mM) | 7 | 38.5 |
| Above, (6.) + CaCl$_2$ (50 mM) | 8 | 82.1 |
| Above, (1.) + Penicillin - Streptomycin (20 μg/ml) | 9 | 90.3 |

*Each value is the mean of duplicate analysis after background activity (3.5%) was subtracted.
**Extract obtained from 38 × 10$^6$ cells/ml.

TABLE 2

The Effect of Four Different Types of Tetracyclines on Rat PMNL Collagenolytic Activity in vitro

| Incubation Mixture | Collagenolytic Activity: % $^{14}$C—collagen gel lyzed |
|---|---|
| PMNL extract* | 39.0 |
| PMNL extract + minocycline** | 4.0 |
| PMNL extract + Achromycin** | 2.0 |
| PMNL extract + Terramycin** | 4.4 |
| PMNL extract + Vibramycin** | 4.5 |
| PMNL extract + ampicillin** | 35.7 |
| PMNL extract + Cefazolin** | 50.0 |

*Extract obtained from 30 × 10$^6$ PMNLs per ml.
**All antibiotics were added to the reaction mixture in a final concentration of 20 ug/ml; this level of antibiotic approximates the concentration of tetracycline found in the periodontal pockets of humans treated with these drugs.

Conclusion

These results (FIGS. I-III and Tables 1-2) demonstrate that: (1) tetracyclines inhibit mammalian collagenolytic enzyme(s) activity and, as a result, inhibit the pathologic loss of collagen (e.g. skin & bone), and (2) tetracyclines have this therapeutic capability through a mechanism unrelated to the drug's antibacterial efficacy. Note that non-tetracycline antibiotics did not have this anti-collagenolytic capability.

EXAMPLE II

Effect of Minocycline Therapy on the Abnormally High Collagenolytic Enzyme Activity in Extracts of Gingiva from Diabetic Rats Rats were made diabetic chemically with the agent streptozotocin. Some of the diabetic rats (half were administered minocycline orally on a daily basis) were killed 15 days, or 28 days, or 56 days after inducing diabetes and the gingiva were dissected, the tissues were extracted, and the extracts partially purified by ammonium sulfate precipitation. The partially purified enzyme preparation from the gingiva of a group of non-diabetic (control) rats, and the diabetic rats, was incubated at 37° C. in vitro with radiolabeled collagen fibrils to assess collagenolytic ennzyme activity.

| Experimental Group | Gingival Collagenolytic Activity (% C$^{14}$—Collagen Degraded) | % Inhibition of Collagenolytic Activity by Minocycline |
|---|---|---|
| Control | 9.1 | — |
| Diabetes — 15 day duration | 50.4 | — |
| Diabetes — 28 day duration | 63.0 | — |
| Diabetes — 56 day duration | 47.8 | — |
| Diabetes + Minocycline, 15 days | 29.0 | 42.5 |
| Diabetes + Minocycline, 28 days | 17.2 | 72.7 |
| Diabetes + Minocycline, 56 days | 10.9 | 77.2 |

Conclusion

Diabetes increased the collagenolytic enzyme activity within the rat gingival tissue. Administering minocycline to the diabetic rats reduced the abnormally high level of collagenolytic enzyme activity within the gingival tissue by 42.5, 72.7 and 77.2%, for rats that were diabetic and administered the drug for 15, 28 and 56 days, respectively. (Again note that the drug did not reduce collagenase activity below normal levels). Also note that the longer the duration of minocycline therapy, the greater the therapeutic effect in reducing the collagenolytic activity.

EXAMPLE III

Human Gingival Crevicular Study (a) 19 year old males 1. analysis

In a separate study involving humans, gingival crevicular fluid (GCF) samples were collected on filter paper strips inserted into 8 interproximal pockets of selected teeth in the maxillary arch of two 19 year-old twin brothers with juvenile-onset (insulin-dependent) diabetes mellitus. Fluid volume was immediately determined on a modified Periotron (Model 6000, Harco Electronics Ltd., Winnipeg, Canada); then incubated with 10 μl ($^3$H-methyl) collagen (20,675 DPM) and 70 μl buffer (50 mM Tris-HCl, pH 7.8, containing 0.2 M sodium chloride and 5 mM calcium chloride). The GCF samples (or reagent blanks or trypsin controls) were incubated at 27° C. for 18 hours with gentle shaking. The reaction was stopped and undigested collagen precipitated by adding 10 μl 0.1 M phenanthroline in dioxane/water (1:1, v/v), 10 μl of nonradioactive methylated carrier collagen (2 mg/ml) in 50 mM Tris-HCl buffer containing 1M NaCl (pH 7.0), and 100 μl dioxane. After mixing, the radiolabeled collagen degradation products were collected by filtration and counted in a liquid scintillation spectrometer (Golub, et. al., 1976, J. Dent. Res., 55, 1049). Using this technique, the reaction blank (no enzyme or GCF added) released about 10% of the total substrate counts; 2–20 ng bacterial collagenase produced a linear increase in the release of radioactive counts from the $^3$H-collagen substrate (the 20 ng level of enzyme degraded 60% of the collagen substrate); and 50 ng trypsin released less than 1% of the counts above blank values. GCF collagenase activity was expressed as units of equivalent activity of vertebrate collagenase (obtained from New England Nuclear, Cat. No. NEK-016); 1 unit was operationally defined as the amount of enzyme that degrades 1 μg of collagen per hour at 27° C.

Four additional GCF samples were collected from other maxillary pockets of the same diabetic twin brothers on filter paper strips, their volume determined (see above), and collagenolytic activity assessed using the same procedure described above but with a different substrate (10 μl of ($^3$H-propionate) collagen, NET-660, New England Nuclear Corp., Boston, Mass., 302,000 DPM).

Half of the 12 GCF samples per subject were activated by pretreatment with 1.04 uM trypsin followed by the addition of a 5-fold molar excess of soybean trypsin inhibitor. Samples were selected to be treated or not treated with trypsin by matching them for Gingival Index (Loe and Silness, Acta. Odont. Scand., 21, 533–551 (1967)), GCF flow, and for pocket depth; the clincal parameters (GI, PD) were measured immediately after GCF collection. All measurements were carried out immediately before antibiotic coverage and after 7 days of treatment with either pencillin G (lg. per day; patient P. D.) or the tetracycline minocycline (200 mg/day; patient K. D.).

a ii) Treatment

In the human study, the adolescent diabetic twin (K. D.) was treated with the tetracycline minocycline (See FIG. IV). Prior to treatment, he demonstrated a greater severity of gingival inflammation (a significantly higher G. I. and a tendency towards increased GCF flow) but similar pocket depth compared to the other diabetic twin (P. D.) who in this study was treated with penicillin. Prior to antibiotic therapy, K. D. also exhibited increased active collagenase and total collagenase (the latter measured after trypsin pretreatment) activities compared to P. D. using either radiolabeled collagen substrate for the assay (see FIG. IV, A and B). Treatment with penicillin, reduced the Gram-positive but increased the Gram-negative organisms in the pockets and had little or no effect on G. I., GCF flow, pocket depth, or on active collagenase; in fact, total enzyme activity appeared to increase, at least with the ($^3$H-methyl) collagen as substrate (see FIG. IV). In contrast, the tetracycline minocycline produced significant reductions in G. I., GCF flow, active and total collagenase, but no decrease in pocket depth, after the 7 days of treatment (FIG. IV). These pockets showed a marked reduction in Gram-negative and a relatively small number of Gram-positive organisms at this time.

(b) Non-diabetic 41 year old male

1. Analysis

The same protocol as in (a) above using the tetracycline minocycline therapy was carried out on a 41 year old non-diabetic male (R. R.), in 12 selected sites in the maxillary arch (GI=1.7±0.2; PD=4.2 mm±0.3), and GCF collagenolytic activity was measured as described above. This patient exhibited deeper periodontal pockets than the 19 year-old diabetic twin brothers. Two additional GCF samples were collected from the same 4 mm pocket, in this patient, before and after minocycline therapy. These samples were incubated with 10 μl $^3$H-collagen for 18 hours (22° C.), then thermally denatured and the collagen subunits and collagenase digestion products were separated by SDS-polyacrylamide gel electrophoresis (Nicoll, et. al., Experientia., 37, 315–317 (1981)). The gels were processed for fluorography (see Sodek, et. al., J. Periodontal. Res., 16, 425–433 (1981)) and exposed to Kodak X A R-5 film for 3 days.

(2) Treatment

Similar to the effect on K. D., treatment of the non-diabetic (R. R.) with minocycline reduced active collagenase by 86%, trypsin-activated collagenase by 59%, GCF flow by 71%, G. I. by 26%, whereas pocket depth was essentially unchanged. The collagen digestion fragments produced by the GCF was analyzed by a fluorograph. The GCF cleavage of the radio-labeled collagen generated $\alpha^A$(a $\frac{3}{4}$ fragment of the collagen molecule) and $\alpha^B$(a $\frac{1}{4}$ fragment) digestion products characteristically produced by vertebrate collagenase. In addition, minocycline therapy: (1) reduced the breakdown of the intact collagen and (2) inhibited the production of the $\alpha^A$ and $\alpha^B$ collagen digestion fragments. Densitometric analysis of the fluorographs demonstrated that the therapy using the tetracycline minocycline reduced the percentage of the total radiolabeled collagenous material present as degradation products.

EXAMPLE IV

Inhibition of Bone Resorption

The direct inhibition of bone resorption (a process involving the dissolution of both the mineral phase and the mostly collagenous organic phase) is demonstrated by the following test procedures.

The technique used to assess bone resorption is based on monitoring the release of radioactive calcium, previously incorporated by embryonic bones in vivo, during organ culture. Pregnant Sprague-Dawley rats were injected subcutaneously with 200 μCi of $^{45}$calcium chloride on the 18th day of gestation. The following day, the animals were killed, the fetuses removed, and the radii and ulnae dissected under aseptic conditions. The bones were pre-incubated under a humidified gas atmosphere (5% carbon dioxide and 95% air) for 24 hours, and this initial medium discarded, to eliminate much of the easily exchangable $^{45}$calcium which does not reflect bone resorption. The bones were then randomly distributed and each bone, either a radius or ulna, was incubated in 0.5 ml of culture media alone or in a media containing parathyroid hormone (PTH: human synthetic 1-34 peptide, Beckman Instruments, Inc., Palo Alto, California) added in a final concentration of 1.0 μg/ml; the experimental bones were incubated in the PTH containing medium to which was added different concentrations (0.2–300 μg/ml) of the antibiotics to be tested. The bones were cultured for 5 days, with the media being changed after day 2, and the incubation terminated. The bones were decalcified in 0.2 ml of 5% trichloroacetic acid and the $^{45}$calcium content of the residual bones and of the culture media was measured as described previously. (Werner and Raisz, Endocrinology, 90, 752 (1972) and Gomes, et. al., Calc. Tiss. Res., 19, 285 (1976)). The $^{45}$calcium released into the media was calculated as a percentage of the total radioactive calcium measured in the bones.

As expected, the non-vital bones released minimal amounts of $^{45}$calcium into the culture media after 2 or 5 days incubation compared to the vital bones (see Table 4), and the addition of PTH to the system increased the loss of radiolabeled calcium by about 90-160% (see Tables 3–5) consistent with previous studies describing the stimulation of bone resorption by this hormone (Stern, et. al., *Proc. Soc. Exptl. Biol. & Med.,* 119, 577 (1965) and Raisz, *J. Clin. Invest.,* 44, 103 (1965)). When non-tetracycline antibiotics, (ampicillin, streptomycin, cefazolin and penicillin) were added in concentrations equal to or exceeding those used for the tetracyclines, they were found to have no detectable effect on PTH-enhanced bone resorption (see Tables 3 & 5). In contrast, minocycline, a tetracycline antibiotic, was found to inhibit $^{45}$calcium release in a dose responsive manner in the absence of any other antibiotics in the media (see Table 3) and its effectiveness on this parameter of bone resorption was unchanged when this semi-synthetic tetracycline was added to the culture media together with penicillin and streptomycin (note that the reduced level of $^{45}$calcium release in the presence of 20 μg/ml minocycline plus 100 or 200 μg/ml penicillin-streptomycin was not significantly different from the level seen with this concentration of minocycline alone; (see Table 3). Like minocycline, two other tetracyclines, doxycycline and tetracycline, also inhibited bone resorption in a dose responsive manner (see Table 4).

PTH is known to stimulate the production of hydrolytic and collagenolytic enzymes in bone in organ culture, and the hormonal effect on lysozomal enzymes appears to precede the release of calcium. Recently, using an organ culture system, the inhibition of collagenase activity was shown to suppress bone resorption (Sakamoto & Sakamoto, *J. Dent. Res.,* 62, Special Issue, 680 (1983)). Thus, the ability of tetracyclines to inhibit bone resorption, is related to its anti-collagenolytic enzyme property.

TABLE 3

The Effect of Minocycline on Parathyroid Hormone (PTH)-Induced Bone Resorption in Organ Culture

| Additions to Culture Media | $^{45}$Calcium in fetal bone released into media (%) | |
|---|---|---|
| | after 2 days incubation[1] | after 5 days incubation[1] |
| None | 19.9 ± 1.5 | 27.6 ± 1.3 |
| PTH alone | 46.1 ± 1.9 | 73.3 ± 1.3 |
| PTH + 0.2 μg/ml minocycline | 42.6 ± 0.6 | 75.6 ± 1.0 |
| PTH + 2 μg/ml minocycline | 44.2 ± 2.1 | 74.7 ± 3.1 |
| PTH + 20 μg/ml minocycline | 22.5 ± 1.6 | 29.2 ± 1.8 |
| PTH + 60 μg/ml minocycline | 19.4 ± 0.9 | 24.5 ± 1.1 |
| PTH + 200 μg/ml minocycline | 17.6 ± 0.4 | 22.3 ± 0.5 |
| PTH + 100 μg/ml Pen.-Strep.[2] | 38.3 ± 1.3 | 75.4 ± 1.3 |
| PTH + 200 μg/ml Pen.-Strep. | 44.7 ± 1.5 | 74.9 ± 1.9 |
| PTH + 2 μg/ml minocycline + 100 μg/ml Pen.-Strep. | 42.9 ± 1.9 | 70.2 ± 3.7 |
| PTH + 2 μg/ml minocycline + 300 μg/ml Pen.-Strep. | 45.7 ± 2.5 | 71.8 ± 3.5 |
| PTH + 20 μg/ml minocycline + 100 μg/ml Pen.-Strep. | 21.5 ± 1.5 | 31.9 ± 2.1 |
| PTH + 20 μg/ml minocycline + 300 μg/ml Pen.-Strep. | 24.0 ± 0.9 | 33.5 ± 1.3 |

[1]Each value represents the mean of 8-10 bone cultures ± S.E.M. Unless otherwise specified, the culture media (which was filter sterilized) contained no antibiotics; any bones or culture media showing evidence of bacterial contamination after the incubation were discarded. In this initial experiment, Pen.-Strep. (penicillin and streptomycin) were found to have no effect on bone resorption, in the presence or absence of minocycline, and, therefore, was added to the culture media in subsequent experiments to reduce the number of culture that had to be discarded due to contamination.
[2]Penicillin-Streptomycin.

TABLE 4

The Effect of Different Tetracyclines on PTH-Induced Bone Resorption in Organ Culture

| Additions to Culture Media | $^{45}$Calcium in Fetal Bone Released into Media (%) | |
|---|---|---|
| | after 2 days incubation[1] | after 2 days incubation[1] |
| None[2] | 9.2 ± 1.0 | 11.5 ± 1.2 |
| None | 27.1 ± 1.0 | 50.8 ± 1.8 |
| PTH alone | 61.6 ± 1.2 | 97.9 ± 0.7 |
| PTH + 0.2 μg/ml minocycline | 54.5 ± 4.1 | 95.1 ± 1.8 |
| PTH + 0.2 μg/ml doxycycline | 56.6 ± 2.0 | 97.1 ± 0.7 |
| PTH + 0.2 μg/ml tetracycline | 58.4 ± 1.3 | 93.0 ± 1.7 |
| PTH + 2.0 μg/ml minocycline | 56.5 ± 2.6 | 93.3 ± 2.6 |
| PTH + 2.0 μg/ml doxycycline | 57.5 ± 2.5 | 93.5 ± 1.7 |
| PTH + 2.0 μg/ml tetracycline | 59.9 ± 1.5 | 97.2 ± 0.8 |
| PTH + 20 μg/ml minocycline | 40.7 ± 0.8 | 50.1 ± 0.8 |
| PTH + 20 μg/ml doxycycline | 30.6 ± 1.7 | 35.3 ± 1.6 |
| PTH + 20 μg/ml tetracycline | 45.0 ± 0.7 | 69.4 ± 3.5 |
| PTH + 200 μg/ml minocycline | 16.4 ± 1.1 | 20.4 ± 1.5 |
| PTH + 200 μg/ml doxycycline | 18.8 ± 1.1 | 28.7 ± 0.8 |
| PTH + 200 μg/ml tetracycline | 14.4 ± 0.4 | 19.8 ± 0.5 |

[1]Each value represents the mean of 9 bone cultures ± S.E.M.
[2]These bones were devitalized (by repeated freezing and thawing) prior to incubation in organ culture.

TABLE 5

The Effect of Ampicillin and Cefazolin on PTH-Induced Bone Resorption in Organ Culture

| Additions to Culture Media | $^{45}$Calcium in fetal bone Released into media (%) | |
|---|---|---|
| | after 2 days incubation[1] | after 5 days incubation[1] |
| None | 22.4 ± 0.7 | 46.7 ± 3.0 |
| PTH alone | 51.2 ± 1.4 | 91.9 ± 1.7 |
| PTH + 6 μg/ml ampicillin | 52.3 ± 1.9 | 92.2 ± 2.0 |
| PTH + 20 μg/ml ampicillin | 52.8 ± 1.7 | 92.6 ± 0.5 |
| PTH + 40 μg/ml ampicillin | 51.9 ± 2.1 | 94.2 ± 1.1 |
| PTH + 60 μg/ml ampicillin | 50.9 ± 1.7 | 93.9 ± 0.7 |
| PTH + 200 μg/ml ampicillin | 50.8 ± 1.8 | 91.4 ± 0.7 |
| PTH + 6 μg/ml cefazolin | 50.8 ± 1.3 | 93.1 ± 0.5 |
| PTH + 20 μg/ml cefazolin | 54.2 ± 1.4 | 93.6 ± 0.4 |
| PTH + 60 μg/ml cefazolin | 54.5 ± 1.2 | 94.6 ± 1.2 |
| PTH + 120 μg/ml cefazolin | 50.3 ± 3.1 | 90.2 ± 3.1 |
| PTH + 200 μg/ml cefazolin | 50.9 ± 1.3 | 92.1 ± 0.6 |

[1]each value represents the mean ± S.E.M. for 8-10 bone cultures.

EXAMPLE VI

Effect of Minocycline Administration on the Collagenolytic Activity in Extracts of Synovial Tissue From Patients with Rheumatoid Arthritis In each of three patients, the diseased joint tissue on one side was surgically removed for therapeutic reasons. The three patients were then administered minocycline orally for 10 days and the diseased joint (synovial) tissue on the opposite side was surgically removed (for therapeutic reasons) after the course of minocycline treatment was completed. The tissues were coded, stored frozen, and analyzed double blind to eliminate any bias in the development of the data. The tissues were dried, the lipid removed, and the collagenolytic activity in the diseased joint tissues extracted and concentrated. Aliquots of the extract from each diseased joint were incubated in vitro with radiolabelled collagen fibrils for 72 hours at 37° C. to assess collagen destructive (collagenolytic) enzyme activity.

| | Synovial Tissue Collagenolytic Activity (% C$^{14}$—collagen degraded) | | |
|---|---|---|---|
| | Before Minocycline Treatment | After Minocycline Treatment | % Reduction by Treatment |
| Patient #1 | 43.0 | 7.8 | 81.8 |
| Patient #2 | 41.0 | 12.8 | 68.8 |
| Patient #3 | 18.6 | 18.0 | 3.3 |

Conclusion

In patients #1 and 2, who exhibited a high level of collagenolytic enzyme activity, the minocycline therapy reduced the activity by 69–82%. In the patient (#3) who had a relatively low level of collagenolytic activity (which, at the beginning of treatment, approximated the level seen in the other two patients after treatment), the minocycline therapy did not reduce collagenolytic activity much further. (Note: This data again indicates that minocycline treatment reduces abnormally high levels of collagenase to nearnormal levels but does not reduce collagenase below normal levels).

EXAMPLE VII

Use of Tetracycline in Controlled-Delivery Devices

A biocompatible polymer such as ethylene vinyl acetate is mixed in 1:3 ratio with tetracycline hydrochloride and melt spun in an Olsen Extrusion Plastometer at 181° C. to provide fibers ca. 0.5 m in diameter and contains 322 ug of tetracycline hydrochloride per cm. (Goodson, et al., 1983, *J. Periodontol.*, 54, 575–579).

The ethylene vinyl acetate fibers are inserted into shallow (ca. 5 mm) periodontal pockets and delivered an initial concentration of 650 ug/ml of tetracycline, and a concentration half time of 13 hours.

In accordance with the above procedure, there may be used polycaprolactone and polyurethane and other polymers in place of ethylene vinyl acetate.

EXAMPLE VIII

Use of Minocyeline containinq Polymer Sheets

Ethylene cellulose polymer (N Type, Hercules, Inc., Delaware, U.S.A.), with or without polyethylene glycol PEG 3000, (BDH, England), is dissolved by slowly adding dry powder to chloroform or ethanol and is vigorously stirred. Minocycline is added after dissolution in the ratio of 10% (w/w). Films of various thicknesses are cast from the chloroform suspension or ethanol solution on glass plates covered by Pergament paper (method of Konig & Goodman, *J. Pharm. Sci.*, 51, 77 (1962)); the film allowed to dry completely and pealed from the plate.

Sheets prepared by the above method can be cut into segments large enough to be inserted into individual peridontal pockets (e.g., about 2×6 mm) and left in place for varying periods of time.

We claim:

1. A method of reducing a pathological excess of mammalian collagenolytic enzyme(s) activity in a mammalian system to substantially normal levels which comprises administering to a mammal in need of anticollagenolytic therapy an amount of a tetracycline which is therapeutically effective in reducing the level of collagenolytic activity substantially to said normal level.

2. A method according to claim 1 wherein the tetracycline administered is tetracycline.

3. A method according to claim 1 wherein the tetracycline administered is minocycline.

4. A method according to claim 1 wherein the tetracycline administered is doxycycline.

5. A method according to claim 1 wherein the pathological excess mammalian collagenolytic activity is manifested by excessive bone resorption.

6. A method according to claim 1 wherein the pathological excess mammalian collagenolytic activity is manifested by periodontal disease.

7. A method according to claim 1 wherein the pathological excess mammalian collagenolytic activity is manifested by rheumatoid arthritis.

8. A method according to claim 1 wherein the pathological excess mammalian collagenolytic activity is manifested by ulceration of the cornea.

9. A method according to claim 1 wherein the pathological excess mammalian collagenolytic activity is manifested by the resorption of skin or other connective tissue collagen.

10. A method according to claim 1 wherein the amount of the tetracycline administered is from 10–100% of the normal antibiotic therapeutic dose of the tetracycline.

* * * * *

(12) EX PARTE REEXAMINATION CERTIFICATE (5230th)
United States Patent
Golub et al.

(10) Number: US 4,666,897 C1
(45) Certificate Issued: Nov. 22, 2005

(54) INHIBITION OF MAMMALIAN COLLAGENOLYTIC ENZYMES BY TETRACYCLINES

(75) Inventors: Lorne M. Golub, Smithtown, NY (US); Thomas F. McNamara, Port Jefferson, NY (US); N. S. Ramamurthy, Smithtown, NY (US)

(73) Assignee: Research Foundation of State University of New York

Reexamination Request:
No. 90/006,752, Aug. 18, 2003

Reexamination Certificate for:
Patent No.: 4,666,897
Issued: May 19, 1987
Appl. No.: 06/566,517
Filed: Dec. 29, 1983

(51) Int. Cl.$^7$ ............................................. A61K 31/65
(52) U.S. Cl. ....................... 514/152; 514/825; 514/900
(58) Field of Search ......................................... 514/152

(56) References Cited

U.S. PATENT DOCUMENTS

| | | | | |
|---|---|---|---|---|
| 4,219,545 A | * | 8/1980 | Collins | ........................ 514/39 |
| 4,276,284 A | * | 6/1981 | Brown | ........................... 514/8 |
| 4,371,465 A | | 2/1983 | McGregor | |

FOREIGN PATENT DOCUMENTS

| | | |
|---|---|---|
| GB | 787882 | 12/1957 |
| GB | 925282 | 5/1963 |

OTHER PUBLICATIONS

Likins et al., "Effect of Fluoride and Tetracycline on Alveolar Bone Resorption in the Rat.", National Institute of Dental Research, NIH, p. 1832, (Jul. 1963).*

Mashimo et al., "In Vitro Evaluation of Antibiotics in the Treatment of Periodontal Disease." Pharmacol. Ther. Dent. vol. 6, pp. 45–56, (1981).*

McNamara et al., "Crevicular Rluid Studies of a Diabetic and Her Non–Diabetic Twin.", Program and Abstracts of Papers, J. of Dental Research, Abstract 1038, vol. 58, Special Issue A (Jan. 1979).*

Williams et al., "Tetracycline Treatment of Periodontal Disease in the Beagle Dog.", J. of Periodontal Research, vol. 17, pp. 358–365, (1982).*

Slots, et al., "Periodontal Therapy in Humans. I. Microbiological and Clinical Effects of a Single Course of Periodontal Scaling and Root Planing, and of Adjunctive Tetracycline Therapy," *J. Periodontol.* 50(10):495–509 (Oct. 1979).

Hellden, et al., "The Effect of Tetracycline and/or Scaling on Human Periodontal Disease," *J. Clin Periodontol*, 6:222–30 (1979).

Herzberg, MC, "Tetracycline as a Therapeutic Adjunct in the Treatment of Periodontal Diseases," *Northwest Dentistry*, 60(3):131–4 (Jun. 1981).

Fasciano, et al., "Periodontal Regeneration with Long Term Tetracycline Therapy," *Quintessence International*, 12(10):1081–8 (Oct. 1981).

Ciancio, et al., "An Evaluation of Minocycline in Patients with Periodontal Disease," *Journal of Periodontology*, 51(9):530–4 (Sep. 1980).

Williams, et al., "Subgingival Microflora of Periodontal Patients on Tetracycline Therapy," *Journal of Clinical Periodontology*, 6:210–21 (1979).

Genco, RJ, "Antibiotics in the Treatment of Human Periodontal Diseases," *J. Periodontol*, 52(9):545–558 (Sep. 1981).

Weeks, DB, "Tetracycline in the Treatment of Periodontal Disease: Review of Current Literature," *J. Am. Dent Assoc.*, 101(6):935–6 (Dec. 1980).

Ciancio, SG "Tetracyclines and Periodontal Therapy," *J. Periodontology* 47(3):155–159 (Mar. 1976).

Gibson, WA "Antibiotics and Periodontal Disease; A Selective Review of the Literature," *Journal of the American Dental Association*, 104(2):213–8 (Feb. 1982).

Kornman, et al., "The Effect of Long Term Low Dose Tetracycline Therapy on the Subgingival Microflora in Refractory Adult Periodontitis," *J. Periodontology* 53 (10):604–610 (Oct. 1982).

Langdon, JD "Antibiotics in General Dental Practice," *British Dental Journal* 136(8):309–16 (Apr. 16, 1974).

Listgarten, et al., "Effect of Tetracycline and/or Scaling on Human Periodontal Disease," *J. Clinical Periodontology*, 5:246–271 (1978).

Mashimo, et al., "In Vitro Evaluation of Antibiotics in the Treatment of Periodontal Disease," *Pharmacol Ther Dent* 6:45–56 (1981).

Scopp, et al., "Tetracycline: A Clinical Study to Determine its Effectiveness as a Long–Term Adjuvant," *J. Periodontology* 51(6):328–330 (1980).

Tanzer, JM Review Article "The Use of Tetracyclines in the Treatment of Periodontal Disease," *J. Conn State Dent Assoc.*, 57(3):105–12 (Aug. 1983).

Weeks, DB "Tetracycline in the Treatment of Periodontal Disease: Review of Current Literature," *Journal—Connecticut State Dental Assoc.* 56:(1)22–4 (Jan. 1982).

Williams, et al., "Subgingival Microflora of Periodontal Patients on Tetracycline Therapy," *J. Clinical Periodontology*, 6:210–221 (1979).

Ciancio et al, "The Effect of Short–Term Administration of Minocycline HCl on Gingival Inflammation and Subgingival Microflora," *J. Periodontol*, 53(9):557–561 (Sep. 1982).

Finch, "Immunomodulating Effects of Antimicrobial Agents," *Journal of Antimicrobial Chemotherapy*, 6:691–694 (1980).

McNamara, et al., "Crevicular Fluid Studies of a Diabetic and Her Non–Diabetic Twin," Program and Abstracts of Papers, *Journal of Dental Research*, Abstract 1038, vol. 58, Special Issue A (Jan., 1979).

(Continued)

*Primary Examiner*—Barbara P. Badio

(57) ABSTRACT

A method of reducing pathologically excessive levels of activity of collagenolytic enzymes in mammals to substantially normal levels by administering 10–100% of the normal antibiotic therapeutic does of a tetracycline is disclosed.

OTHER PUBLICATIONS

Likins, et al., "Effect of Fluoride and Tetracycline on Alveolar Bone Resorption in the Rat," *National Institute of Dental Research, National Institutes of Health* p. 1532 (Jul. 29, 1963).
Guerrant, "Chlortetracycline and Bone Demineralization in the Rachitic Rat," *Proceedings of the Society for Experimental Biology and Medicine*, 113:268–270 (May–Aug.–Sep., 1963).
Dreisbach, et al., "Induction of Collagenase Production in Vibrio B–30," *Journal of Bacteriology*, 135(2):521–527 (Aug. 1978).
Williams, et al., "Tetracycline Treatment of Periodontal Disease in the Beagle Dog," *Journal of Periodontal Research*, 17:358–365 (1982).
Williams, et al., "Preliminary Observation on the Inhibitory Effect of Tetracycline on Alveolar Bone Loss in Beagle Dogs," *J. Periodontal Res.*, 14:341–351 (1979).
Jeffcoat, et al., "Tetracycline Treatment of Periodontal Disease in the Beagle Dog," *Journal of Periodontal Research*, 17:545–551 (1982).
Williams, et al., "Tetracycline Treatment of Periodontal Disease in the Beagle Dog," *Journal of Periodontal Research*, 16:659–665 (1981).
Williams, et al., "Tetracycline Treatment of Periodontal Disease in the Beagle Dog," *Journal of Periodontal Research*, 16:666–674 (1981).
Valcavi, et al., *Chemical Abstracts*, 95:6899h, (1981).
Brandt, et al., *Chemical Abstracts*, 92:163746m, (1979).
Glatz, et al., *Chemical Abstracts*, 91:20178w, (1979).
Muxfeldt, *Chemical Abstracts*, 76:140344j, (1972).
Bitha, et al., *Chemical Abstracts*, 72:43253P, (1970).
Myl'nikova, *Chemical Abstracts*, 86:66138h, (1976).
Plakunov, *Chemical Abstracts*, 80:104410b, (1973).
Goodson, et al., "Monolithic Tetracycline–containing Fibers for Controlled Delivery to Periodontal Pockets," *J. Periodontol.* 54(10):575–579 (Jan. 1983).
"Zyderm Collagen Treatments," Collagen Corporation, Advertisement, (Dec. 1981).
Golub, et al., "Minocycline Therapy Inhibits the Abnormal Gingival Collagenolytic Activity During Experimental Diabetes," *Journal of Dental Research*, 62:290, Abstract 1085, (1983).
Brown et al., "Rheumatoid Arthritis in the Gorilla: A Study of Mycoplasma–Host Interaction of Pathogenesis and Treatment," *Comparative Pathology of Zoo Animals*, 259–266 (1980).
Berman, M.B., "Collagenase and Corneal Ulceration," 8:141–174, (1980).
Addy et al., "The Development and in Vitro Evaluation of Acrylic Strips and Dialysis Tubing for Local Drug Delivery," *J. Periodontal*, 693–699, (Nov. 1982).
Kanig & Goodman, *J. Pharm. Sci.*, 51:77–83 (1962).
Loe and Silness, *Acta. Odont. Scand.*, 21:533–551 (1963).
Raisz, *J. Clin. Invest.*, 44(1):103–116 (1965).
Stern et al., *Proc. Soc. Exptl. Biol. & Med.*, 119:577–583 (1965).
Bissada, et al., *Periodontics*, 4(5):233–240 (1966).
Finestone and Boorujy, *Diabetes*, 16(5):336–340 (1967).
Stralfors, et al., *Archs. Oral. Biol.*, 12:1213–1216 (1967).
Wener, et al., *Endocrinology*, 90(3):752–9 (1972).
Ramamurthy et al., *J. Periodontal Res.*, 9:199–206 (1974).
Golub, et al., "Some Characteristics of Collagenase Activity in Gingival Crevicular Fluid and Its Relationship to Gingival Diseases in Humans," *J. Dent Res.*, 55(6):1049–1057 (Nov.–Dec. 1976).
Gomes, et al., *Calcif. Tiss. Res.*, 19:285–93 (1976).
Crawford, et al., *J. Periodontal Res.*, 13:316–325 (1978).
Golub et al., *J. Dent. Res.*, 57:520–525 (1978).
Golub, et al., *Biochim Biophys. Acta.*, 534:73–81 (1978).
Heijl, et. al., *J. Periodontal Res.*, 15:405–419 (1980).
Genco, et al., *J. Dent. Res.*, 60, Special Issue A, Abstract 872 (1981).
Schneir and Golub, (Streptozotocin: Fundamentals and Therapy) ED. M.K. Agarwal, Elsevier/North–Holland Biomed Press, Chapter 12, pp 161–182, 1981.
Sellers and Murphy, *Int. Rev. Conn. Tiss. Res.*, 9:151–189 (1981).
Sodek, et. al., *J. Periodontal Res.*, 16:425–433 (1981).
Nicoll, et al., *Experientia*, 37:315–317 (1981).
Cianciola, et al., *J.A.D.A.*, 104:653–660 (1982).
Golub, et al., *Infect. Immun*, 37:1013–1020 (1982).
Kaplan, et al., *J. Dent. Res.*, 61, Special Issue, Abstract 872 p. 275 (1982).
McNamara et al., *Archs. Oral Biol.*, 27:217–223 (1982).
Ramamurthy and Golub, *J. Periodontal Res.*, 18:23–30 (1983).
Sakamoto and Sakamoto, *J. Dent. Res.*, 62, Special Issue, Abstract 272 p. 680 (1983).
Krook et al., "Experimental Studies on Osteoporosis," *Methods Achiev Exp Pathol*; 7:72–108 (1975).
Rosemberg, J. "Action of Doxycycline (Vibramycin) in Dental Diseases," (Acao da doxiciclina (vibramicina) em afeccoes odontologicas) *Revista da Associacao Paulista de Cirurgioes Dentista*, 23(2):55–61 (Mar.–Apr. 1969) (Brazil) (English Translation).
Gutierrez G. C. "Clinical Trial with the Use of Doxycycline in Dentristry," (Ensayo clinico con doxiciclina en odontoestomatologia) *Anales Espanoles de Odontoestomatologia*, 28(5):372–7 (Sep.–Oct. 1969) (Spain) (English Translation).
Pes, I "Treatment of Mouth Diseases with Doxycycline," (Trattamento di affezioni stomatologiche con doxiciclina) *Rivista Italiana di Stomatologia*, 26(9):691–5 (1971)(Italy) (English Translation).
Wedler, A "Topical Application of Oxytetracycline in the Treatment of Ulcerative Gingivitis and Stomatitis," (Miejscowe stosowanie oxyterracyny w leczeniu wrzodziejacego zapalenia dziasel I blony sluzowej jamy ustnej) *Czasopismo Stomatologiczne*, 25(1):103–12 (1972). (Poland) (English Translation).
Abud, et al., J "Doxycycline in Dental Infections," (Doxiciclina en infecciones odontologicas) *Odontologia Chilena*, 22(111):19–21 (Jan.–Jun. 1974). (Chile). (English Translation).
Bruno, et al., "Clinical Comparative Study between Rifamycin, Doxycycline and Amoxicillin in the Treatment of Odontogenic Bone Inflammation," (Indagine clinica comparative fra rifampicina, doxiciclina e amoxicillina nel trattamento degli osteofilammoni odontogeni) *Rivista Italliana Di Stomatologtia*, 51(7–8): 635–43 (1982). (Italy). (English Translation).
Gangarosa et al., Pharmacotherapeutics in Dentistry, Chapter 28 ("Tetracycline") pp. 281–285, Appleton–Century–Crofts, publishers, Norwalk, Conn. (1983).
Golub, et al., Journal of Periodontal Research, 20, 12–23 (1985).

* cited by examiner

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–10 is confirmed.

* * * * *